US012653536B2

(12) United States Patent
Zheng et al.

(10) Patent No.: US 12,653,536 B2
(45) Date of Patent: Jun. 16, 2026

(54) EPINEURIUM REPAIR DEVICE AND METHODS OF USE THEREOF

(71) Applicant: ORTHOCELL LIMITED, Murdoch (AU)

(72) Inventors: Minghao Zheng, City Beach (AU); Paul Anderson, Nedlands (AU)

(73) Assignee: Orthocell Limited, Western Austrlia (AU)

( * ) Notice: Subject to any disclaimer, the term of this patent is extended or adjusted under 35 U.S.C. 154(b) by 307 days.

(21) Appl. No.: 18/288,165

(22) PCT Filed: Apr. 27, 2022

(86) PCT No.: PCT/AU2022/050386
§ 371 (c)(1),
(2) Date: Oct. 24, 2023

(87) PCT Pub. No.: WO2022/226590
PCT Pub. Date: Nov. 3, 2022

(65) Prior Publication Data
US 2024/0206877 A1 Jun. 27, 2024

(30) Foreign Application Priority Data
Apr. 27, 2021 (AU) ................................ 2021901244

(51) Int. Cl.
*A61B 17/11* (2006.01)
*A61L 27/24* (2006.01)

(52) U.S. Cl.
CPC .......... *A61B 17/1128* (2013.01); *A61L 27/24* (2013.01); *A61L 2430/32* (2013.01)

(58) Field of Classification Search
CPC ......... A61B 17/1128; A61B 2017/1132; A61L 27/24; A61L 2430/32; A61L 2300/414
See application file for complete search history.

(56) References Cited

U.S. PATENT DOCUMENTS 6,102,921 A     8/2000  Zhu et al.
2018/0064931 A1*  3/2018  Clements ............... A61B 5/388
(Continued)

FOREIGN PATENT DOCUMENTS

CN     101579247 B    11/2009
CN     108853583      11/2018
(Continued)

OTHER PUBLICATIONS

Amado et al., (2010) "Effects of collagen membranes enriched with in vitro-differentiated N 1 E-115 cells on rat sciatic nerve regeneration after end-to-end repair" Journal of NeuroEngineering and Rehabilitation, 7:7, 1-13.
(Continued)

*Primary Examiner* — Carlos A Azpuru
(74) *Attorney, Agent, or Firm* — Todd W. Esker; Bozicevic, Field & Francis LLP

(57) ABSTRACT

The subject invention relates generally to the repair of severed or damaged nerve and/or epineurium in a patient in need of such treatment. In particular, the present invention provides devices and methods of repairing severed or damaged nerve and/or epincurium. In some embodiments, a device is provided for the in vivo repair of severed or damaged nerve and/or epineurium comprising: a pliable collagen membrane comprising a first surface and a second surface, said first surface having a plurality of protruding collagen bundles and said second surface comprising a plurality of apertures, said apertures and said collagen bundles arranged to form a self-engaging attachment when said first surface and said second surface are placed together.

11 Claims, 10 Drawing Sheets

Repair device wrapped around nerve stumps

Nerve stump (12) (Proximal end)
Repair site (20)
Nerve stump (12) (Distal end)
Non-resorbable Sutures (18)
Repair device (10)
Epineurial microsutures (16)

(56) References Cited

U.S. PATENT DOCUMENTS

| | | |
|---|---|---|
| 2018/0140742 A1 | 5/2018 | Uchida et al. |
| 2019/0314132 A1 | 10/2019 | Deister et al. |
| 2019/0381144 A1 | 12/2019 | Friel |
| 2020/0384157 A1 | 12/2020 | Ghanbari et al. |

FOREIGN PATENT DOCUMENTS

| | | |
|---|---|---|
| CN | 109260459 | 1/2019 |
| WO | 2014-074134 A1 * | 5/2014 |
| WO | WO 2014/074134 | 5/2014 |

OTHER PUBLICATIONS

Pertici et al., (2014) "Comparison of a collagen membrane versus a fibrin sealant after a peroneal nerve section and repair: a functional and histological study" Acta Neurochirurgica, 56:8 1577-1590.

Yoo et al., (2020) "Augmented peripheral nerve regeneration through elastic nerve guidance conduits prepared using a porous PLCL membrane with a 3D printed collagen hydrogel" Biomaterials Science, 8:22, 6261-6271.

Cui, et al., "Collagen scaffolds modified with CNTF and bFGF promote facial nerve regeneration in minipigs", Biomaterials, 35;7819-7827, 2014.

* cited by examiner

Repair device wrapped around nerve stumps

Nerve stump (12) (Proximal end)　　　Repair site (20)　　　Nerve stump (12) (Distal end)

Non-resorbable Sutures (18)

Repair device (10)　　　Epineurial microsutures (16)

A                                                        B

EPINEURIUM REPAIR DEVICE AND METHODS OF USE THEREOF

PRIORITY CLAIM AND RELATED APPLICATION

This application claims priority to Australian Provisional Patent Application No. 2021901244, filed Apr. 27, 2021, which is incorporated by reference herein in its entirety.

FIELD OF THE INVENTION

The subject invention relates generally to the repair of severed or damaged nerve and/or epineurium in a patient in need of such treatment.

BACKGROUND OF INVENTION

Nerves carry the peripheral processes (or axons) of neurons. The neuronal cell bodies reside in the spinal cord (motor neurons), in ganglia situated along the vertebral column (spinal sensory ganglia) or in ganglia found throughout the organs of the body (autonomic and enteric ganglia). A nerve consists of axons, Schwann cells and extensive connective tissue sheaths. The outer covering, the epineurium, is made of collagenous connective tissue that cushions the fascicles from external pressure and surrounds the perineurium. The perineurium surrounds the individual fascicles and, together with endothelial cells in the endoneurial microvessels, functions as the blood-nerve barrier. The endoneurium lies inside the perineurium and consists of collagenous tissue that surrounds the Schwann cells and axons. A fascicular group consists of two or more fascicles surrounded, respectively, by perineurium and epineurium. The topography of nerves is constant distally, with a group of fascicles being either sensory or motor. The neuron consists of a soma (cell body) and an axon, which can be several feet long.

Damage to nerves can be caused by physical injury or swelling (e.g., carpal tunnel syndrome), autoimmune diseases (e.g., Guillain-Barre syndrome), infection (neuritis), diabetes or failure of the blood vessels surrounding the nerve. Nerve injuries are a major source of chronic disability. Poor management of nerve injuries is associated with muscle atrophy and can lead to painful neuroma when severed axons are unable to re-establish continuity with the distal nerve. Although nerves have the potential to regenerate after injury, this ability is strictly dependent upon the regenerating nerve fibres making appropriate contact with the severed nerve segment.

Repairing damaged nerves is hampered by several factors, including damage to the protective sheathing that surrounds nerves (epineurium), gaps between the proximal and distal stumps of severed nerves and the limited ability of damaged nerves to regenerate.

A variety of sutureless nerve repair methods have been explored including the use of biological glues. The advantages of gluing techniques include the potential for simple application and rapid repair time. Unfortunately, biological glues like fibrin glue have insufficient adhesive and tensile strength to ensure a secure nerve union for most nerve repairs without the assistance of devices like tubes or conduits.

Tubes or conduits for guiding peripheral nerve regeneration are commonly made of materials such as polylactide, polylactide/polyglycolide copolymers, acrylic copolymers, performed mesothelial tubes or various other synthetic polyesters. The shortcomings of using a tube or conduit made of these materials include, for example, immune response, induction of scar tissue, and difficulty in application. For example, many of these conduits are too rigid and not readily adapted for in vivo use.

One of the major problems in repairing nerves is repairing the epineurium. It is often found that the epineurium is poorly healed using the currently available devices and techniques. While these devices have been shown to be capable of filling voids or gaps in nerves or even coaptation of severed nerves the repaired nerves often have issues with scar tissue: fibrous adhesion to the surrounding soft tissue in the patient; inflammation, a lack of neurofilament growth and no axon regeneration across the repair site.

Thus, there remains a need for materials and techniques that provide a safe, effective means of repairing severed or damaged nerves and/or epineurium in patients.

SUMMARY OF THE INVENTION

In a first aspect, the present invention provides a device for the in vivo repair of severed or damaged epineurium comprising: a pliable collagen membrane comprising a first surface and a second surface, said first surface having a plurality of protruding collagen bundles and said second surface comprising a plurality of apertures, said apertures and said collagen bundles arranged to form a self-engaging attachment when said first surface and said second surface are placed together.

In a second aspect, the present invention provides an in vivo method of repairing severed or damaged epineurium comprising:

(i) providing a device for the in vivo repair of severed or damaged epineurium comprising: a pliable collagen membrane comprising first surface and a second surface, said first surface having a plurality of protruding collagen bundles and said second surface comprising a plurality of apertures, said apertures and said collagen bundles arranged to form a self-engaging attachment when said first surface and said second surface are placed together;

(ii) wrapping said pliable membrane around at least a lengthwise portion of a severed or damaged nerve in situ, wherein said severed or damaged nerve comprises a severed or damaged epineurium, and (iii) allowing said device to remain in place for a period of time until said severed or damaged epineurium is repaired.

In a third aspect, the present invention provides a device for the in vivo repair of severed or damaged nerves comprising: a pliable collagen membrane comprising a first surface and a second surface, said first surface having a plurality of protruding collagen bundles and said second surface comprising a plurality of apertures, said apertures and said collagen bundles arranged to form a self-engaging attachment when said first surface and said second surface are placed together.

In a fourth aspect, the present invention provides an in vivo method of repairing severed or damaged nerves comprising:

(i) providing a device for the in vivo repair of severed or damaged nerves comprising: a pliable collagen membrane comprising a first surface and a second surface, said first surface having a plurality of protruding collagen bundles and said second surface comprising a plurality of apertures, said apertures and said collagen bundles arranged to form a self-engaging attachment when said first surface and said second surface are placed together;

(ii) wrapping said pliable membrane around at least a lengthwise portion of a severed or damaged nerve in situ, and (iii) allowing said device to remain in place for a period of time until said severed or damaged nerve is repaired.

In a fifth aspect, the present invention provides an in vivo nerve transfer method comprising:

(i) providing a donor nerve which comprises epineurium;

(ii) providing a device for the in vivo repair of severed or damaged nerve comprising: a pliable collagen membrane comprising a first surface and a second surface, said first surface having a plurality of protruding collagen bundles and said second surface comprising a plurality of apertures, said apertures and said collagen bundles arranged to form a self-engaging attachment when said first surface and said second surface are placed together;

(iii) suturing in place said donor nerve and then wrapping said pliable collagen membrane around at least a lengthwise portion of the donor and recipient nerves to encase said epineurium, and (iv) allowing said device to remain in place for a period of time until coaptation of the nerve has occurred.

In some embodiments, the apertures and the collagen bundles are configured to interlock with each other when the first surface and the second surface are placed together.

In some embodiments, the membrane is of an elongated configuration.

In some embodiments, the pliable collagen membrane is configured to be able to be wrapped around at least a lengthwise portion of a mammalian nerve in situ, in a manner where the first and the second surfaces are able to be placed together to self-attach to each other.

In some embodiments, the mammalian nerve comprises severed or damaged epineurium, wherein the pliable collagen membrane is less than 200 microns thick, and wherein the device when wrapped around the severed or damaged nerve is capable of repairing the severed or damaged epineurium in less than 4 weeks.

In some embodiments, the period of time is sufficient to enable the device to become successfully integrated into the nerve or epineurium being repaired. Successful integration can be assessed visually or histologically.

In some embodiments, the damaged nerve or damage epineurium results in a defect site.

In a sixth aspect, the present invention provides a repair kit for the in vivo repair of nerve and/or epineurium comprising:

(i) a device for the in vivo repair of severed or damaged nerve and/or epineurium comprising: a pliable collagen membrane comprising a first surface and a second surface, said first surface having a plurality of protruding collagen bundles and said second surface comprising a plurality of apertures, said apertures and said collagen bundles arranged to form a self-engaging attachment when said first surface and said second surface are placed together;

(ii) a sterile container for retaining said device;

(iii) and instructions for attaching said device to a nerve and/or epineurium in need of repair.

Optionally, the repair kit will further comprise one or more of the following: sutures: forceps, suture needle, fibrin glue and accessory tools for tissue approximation e.g. clips, standard weights, aspiration apparatus, and compression gauges.

BRIEF DESCRIPTION OF THE DRAWINGS

The file of this patent contains at least one drawing executed in colour. Copies of this patent with colour drawings(s) will be provided by the Patent and Trademark Office upon request and payment of the necessary fee.

DESCRIPTION OF THE PREFERRED EMBODIMENTS OF THE INVENTION

Figure 1:
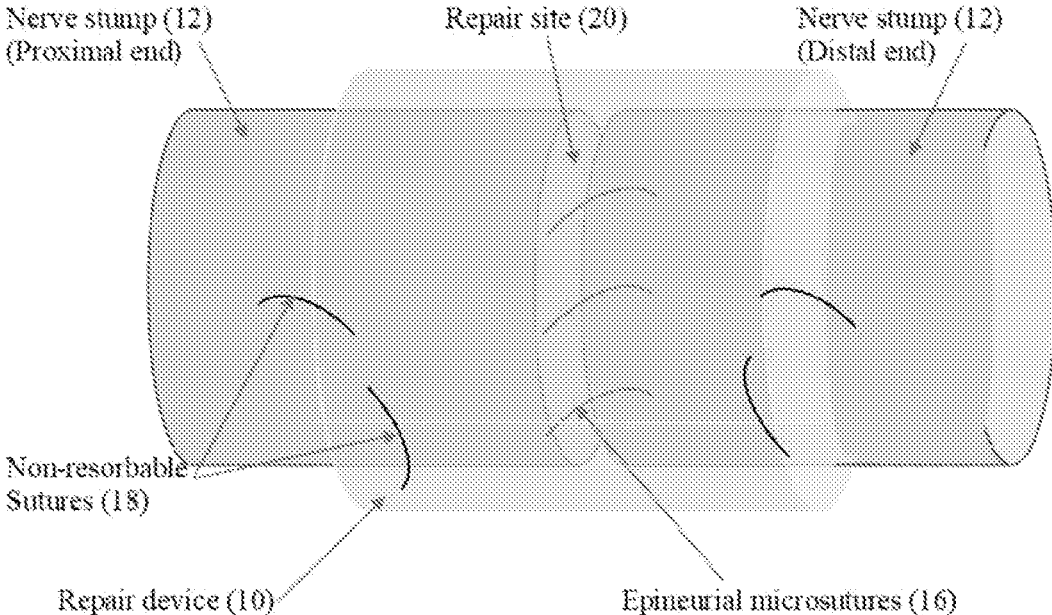
FIG. 1 shows the surgical procedure in the preclinical study of the nerve repair device (10) of the present invention. The sciatic nerve was completely transected, then repaired with epineurial microsutures (16). The repair site (20) was encased by the nerve repair device (10) of the present invention, which was attached to the nerve stumps (12) using non-resorbable sutures (18) on either side of the repair site (20).

The subject invention provides devices and methods for the repair of severed or damaged nerve and/or epineurium in a patient in need of such treatment. In the description that follows, a number of terms related to medical devices and nerve repair are utilized. In order to provide a clear and consistent understanding of the specification and claims, including the scope to be given such terms, the following definitions are provided.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y". As used herein, phrases such as "from about X to Y" mean "from about X to about Y".

The term "about" as used herein refers to a deviation in the value following the term by 10% above or below. For example, reference to about 70% ethanol includes ranges between 63% and 77% i.e. 10% below or above the 70% value. This includes 64%, 65%, 66%, 67%, 68%, 69%, 70%, 71%, 72%, 73%, 74%, 75%, 76% and 77% ethanol.

The term "patient" as used herein, describes any mammal to which the devices and methods of the present invention are applied. Mammalian species that can benefit from the disclosed devices and methods include, but are not limited to, humans, apes, chimpanzees, orangutans, monkeys: domesticated animals (e.g., pets) such as dogs, cats, guinea pigs, hamsters: veterinary uses for large animals such as cattle, horses, goats, sheep: and any wild animal for veterinary purposes. Human or non-human animal patients can range in age from neonates to elderly.

The term "surgeon" as used here is merely for literary convenience. The term should not be construed as limiting in any way. The devices, apparatuses, methods, techniques and/or procedures of the subject invention could be utilized by any person desiring or needing to do so and having the necessary skill and understanding of the invention.

The terms "nerve" and "nerve tissue" as used herein interchangeably refers to the entire structure of a mammalian nerve. It is well understood by those skilled in the art that a nerve consists of axons, Schwann cells and extensive connective tissue sheaths. The outer covering, the epineurium, is made of collagenous connective tissue that cushions the fascicles from external pressure and surrounds the perineurium. The perineurium surrounds the individual fascicles and, together with endothelial cells in the endoneurial microvessels, functions as the blood-nerve barrier. The endoneurium lies inside the perineurium and consists of collagenous tissue that surrounds the Schwann cells and axons. Thus, when reference is made to the "repair" of damaged or severed nerves it equally refers to the damage or severance of structures such as the endoneurium, perineurium and the epineurium.

The term "repair" or "repairing" or grammatical equivalents thereof are used herein to describe the in vivo effects of the device and methods of the invention on nerves and especially epineurium in a patient. "Repair" refers to the in vivo formation of new nerve and/or epineurium tissue which is sufficient to at least partially fill a void or structural discontinuity at a defect site. The term "repair" further encompasses the successful integration of the device of the present invention into the nerve and/or epineurium without causing undue scar tissue formation or fibrous adhesion of the repaired nerve to the surrounding tissue of the patient. Repair does not however, mean or otherwise necessitate, a process of complete healing or a treatment, which is 100% effective at restoring a nerve or its epineurium to its pre-defect physiological/structural/mechanical state.

The terms "defect," "defect site," "nerve defect," "epineurium defect" or "nerve defect site," or "epineurium defect site", all refer to disruptions in nerve and/or epineurium. A defect results in a nerve and/or epineurium performing at a suboptimal level or being in a suboptimal condition. A nerve or epineurium defect can assume the configuration of a "void", which is understood to mean a three-dimensional defect such as, for example, a gap, cavity, hole or other substantial disruption in the structural integrity of the nerve or epineurium. In certain embodiments, the defect is such that it is incapable of endogenous or spontaneous repair. A nerve or epineurium defect can be the result of accident, disease, and/or surgical manipulation.

The phrase "severed or damaged epineurium" refers to nerve that comprises an epineurium defect that needs repair as defined herein. The epineurium defect could be complete in that the entire nerve including the entire epineurium has been severed.

The term "device" is used herein interchangeably with the phrase "device for the in vivo repair of severed or damaged nerve" or "device for the in vivo repair of severed or damaged epineurium" and refers to a physical article comprising a "pliable collagen membrane" that can be used to aid the in vivo repair of severed or damaged nerves and/or epineurium within the patient.

The term "successful integration" as used herein refers to the ability of the device of the present invention to incorporate into the nerve defect or epineurium defect after "a period of time". Persons skilled in the art would appreciate how "successful integration" can be assessed, however, briefly one or more of the following are examples of successful integration: (i) the repair device does not protrude out of alignment with the epineurium and/or nerve to which it was attached following an appropriate period of time after attachment: (ii) there is little or no scar tissue formation at the site of attachment after an appropriate period of time after attachment: (iii) there is little or no fibrous adhesion of the repaired nerve to the surrounding soft tissue in the patient: (iv) histological examination shows new, vascularised epineurium-like tissue at the nerve repair site: (v) there is no evidence of inflammatory reaction following an appropriate period of time after attachment: (vi) abundant neurofilaments are detected adjacent to the new epineurium tissue by immunohistochemistry: (vii) well-organised nerve fibres are observed distal to the nerve repair site: and (viii) evidence of successful axon regeneration across the repair site.

The term "pliable collagen membrane" as used herein refers the collagen membrane used in the devices of the present invention. The collagen membrane is pliable not merely flexible. There are many devices for the repair of nerves and other tissue that are described in the literature as flexible e.g. porcine small intestinal submucosa (SIS); however, the collagen membrane used in the present invention is more than simply flexible. The collagen membrane is sufficiently pliable to be readily or easily bent not just capable of bending without breaking (flexible). The pliability of the collagen membrane in the devices of the present invention allows them to be easily wrapped around a damaged, but intact nerve, in situ, without breaking or causing damage to the nerve.

In some embodiments, the pliable collagen membrane is less than 200 microns thick. In further embodiments, the pliable collagen membrane is between 100 micron and 200 microns thick. In still further embodiments, the pliable collagen membrane is less than 100 microns thick. In still further embodiments, the pliable collagen membrane is less than 75 microns thick.

The pliable collagen membrane of the present invention comprises type I collagen. Type I collagen is composed of two .alpha. 1 chains and one .alpha.2 chain. In some embodiments, the pliable collagen membrane of the present invention comprises greater than 80% type I collagen. In other embodiments, the collagen membrane comprises at least 85% type I collagen. In still other embodiments the collagen membrane comprises greater than 90% type I collagen. The pliable collagen membrane of the present invention further comprises type III collagen.

Figure 7:
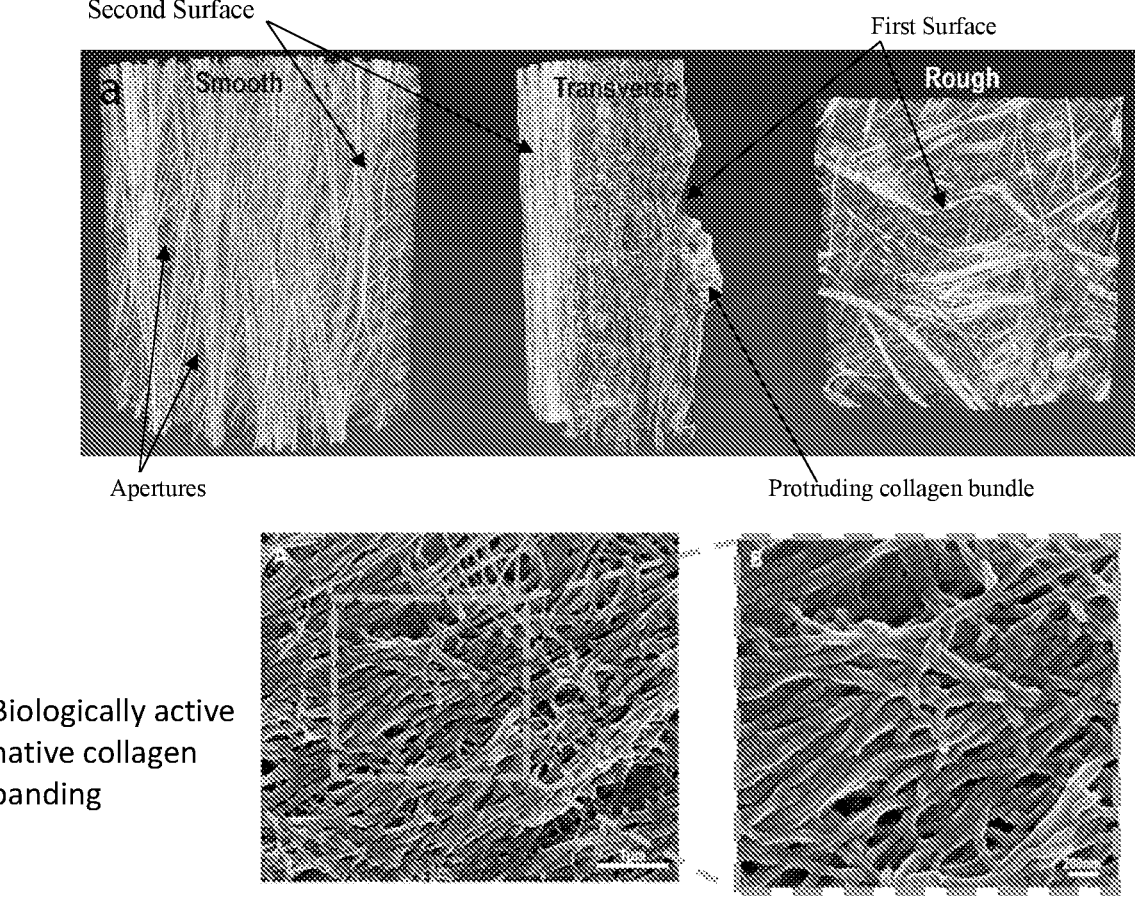
FIG. 7 shows the ultra-structure of the nerve repair device of the present invention. It can be seen that the pliable collagen membrane within the nerve repair device of the present invention comprises a bilayer comprising a first surface which is smooth and a second surface that is rough. The first surface and second surface are capable of engaging to lock together.
Figure 8:
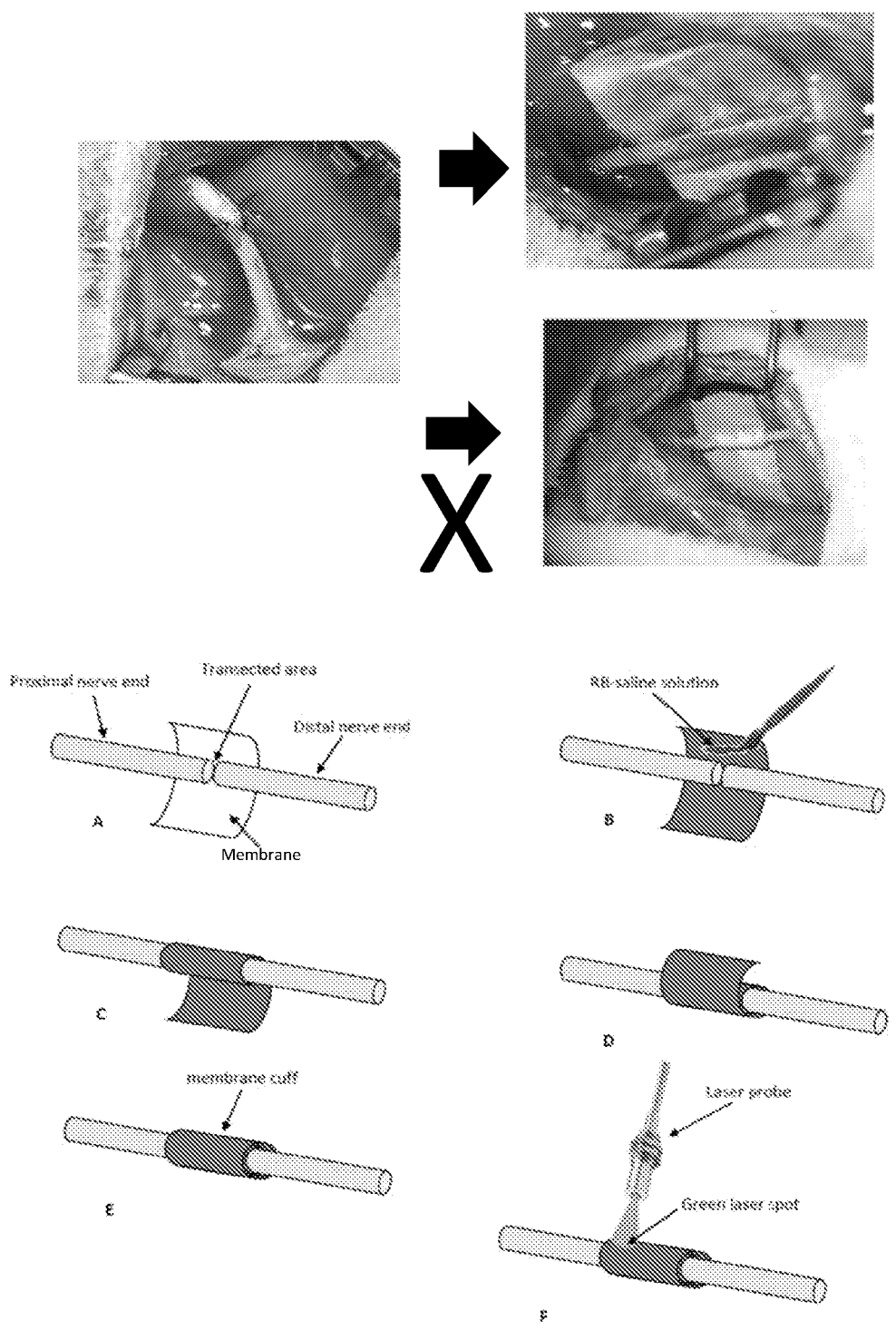
FIG. 8 shows that the collagen bundles on the rough side of the nerve repair device of the present invention are able to insert into the holes on the smooth side of the device such that when they are overlapped under moist conditions like that found in vivo, the generate an interlocking adhesive surface (similar to the action of VELCRO™) to wrap and hold the nerve in shape. This enables the nerve repair device of the present invention to protect nerve from soft tissue compression and act as a barrier structure like epineurium for the protection of nerve.
Figure 9:
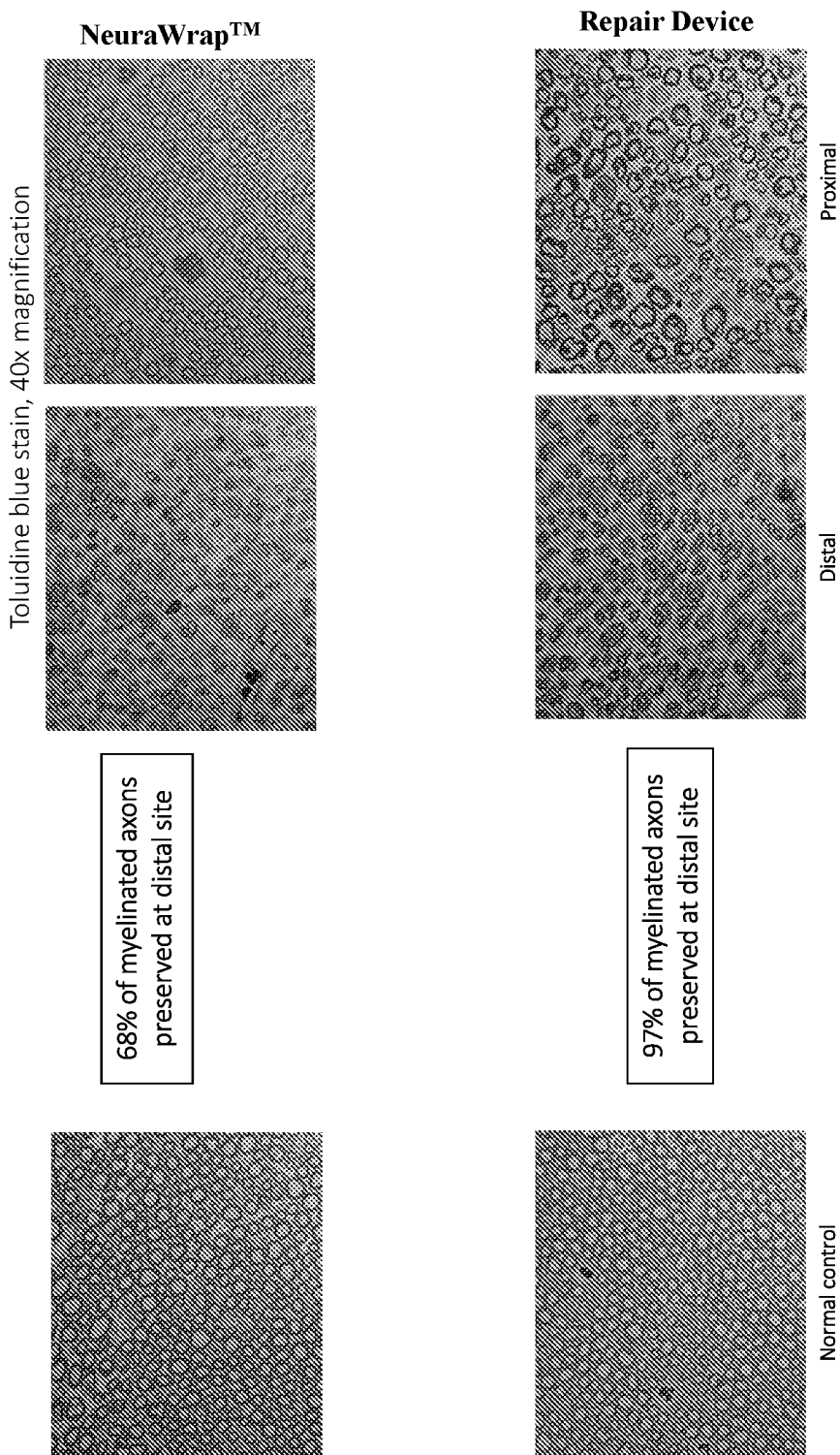
FIG. 9 shows the measurement of myelinated axons at distal site. It can be seen that the nerve repair device of the present invention induced preservation of 97% of axons as compared to 68% in the NEURAWRAP™ product after 4 weeks.

The pliable collagen membrane of the present invention comprises two surfaces (bilayer). The first surface comprises a plurality of collagen bundles that protrude from the surface of the membrane. As shown in FIG. 7, panel A (transverse section) these collagen bundles extend from the first surface. Viewing the pliable collagen membrane from a superior view (front on) it appears to be rough, which is caused by the presence of the plurality of collagen bundles. Conversely, the second surface of the pliable collagen membrane appears smooth when viewed inferior (from the bottom). As shown in FIG. 7, panel A (smooth) there is no collagen bundles present on the second surface.

The term "collagen bundles" as used herein refer to a mass of collagen fibres which are composed of three polypeptide chains that intertwine to form a right-handed triple helix. The collagen bundles are generally arranged along the direction of the first surface. These collagen bundles are predominately found in dense connective tissue found in tendons, ligaments and the dermis of mammals. Dense connective tissue is distinct from "loose connective tissue". Loose connective tissue is characterised by loosely arranged fibres and an abundance of cells and is present, for example, beneath the epithelia that covers body surfaces and lines internal organs.

The second surface of the pliable collagen membrane predominately comprises loose connective tissue comprising type I and type III collagen fibres, which provides a plurality of apertures. These apertures are essentially "voids" or "gaps" between the collagen "microfibrils," "fibrils," and "fibres" found in loose connective tissue. Microfibrils are about 3.5 to 50 nm in diameter. Fibrils are about 50 nm to 50 .mu·m in diameter. Fibres are above 50 .mu·m in diameter.

While the pliable collagen membrane of the present invention is predominately made of type I and type III collagen it would be appreciated that other materials might be included in the pliable collagen membrane as long as these did not adversely affect the repair effects of the pliable collagen membrane as described infra.

Other possible materials include, but are not limited to, hydroxyapatite or drugs that facilitate tissue growth: growth factors such as basic fibroblast growth factor, tumour growth factor beta, bone morphogenic proteins, platelet-derived growth factor, and insulin-like growth factors: chemotactic factors such fibronectin and hyaluronan; and extracellular matrix molecules such as aggrecan, biglycan, and decorin.

The "dense connective tissue" and the "loose connective tissue" is readily obtained from "collagen-containing tissue" such as skin, muscle and the like which can be isolated from a mammalian body that contains collagen. In some embodiments, the tissue containing dense and loose connective tissue is isolated from a tendon.

Typically, the device of the present invention will be attached at the site of the defect and secured in place. Factors such as the size of the nerve or epineurium defect will dictate how much of the nerve or epineurium will be required to be covered by the device of the present invention. The surgeon or other persons skilled in the art will be able to determine what portion of nerve or epineurium is covered. In some embodiment, at least a lengthwise portion (along the nerve or epineurium) will be covered by the repair device. Typical knowledge regarding the placement of repair devices would be required. For example, there is no requirement to encase the entire nerve or epineurium with the repair device. Equally, merely covering the defect site would be insufficient protection of the repair site.

The term "wrapping" as used herein refers to the preferred process of attachment of the pliable collagen membrane to the severed or damaged nerve or epineurium. Wrapping is particularly useful when the nerve, containing the epineurium defect site, is intact i.e. not severed. In this situation wrapping the device around the nerve to encase the defect site is the best option for attachment. Wrapping can also be used when the nerve or epineurium are severed as is the case during nerve transfer. In this case other attachment means might be used to supplement the attachment as described supra.

By wrapping the pliable collagen membrane around a nerve or epineurium defect site, the first surface and the second surface can be placed together i.e. overlapped. The pliable collagen membrane is typically wrapped so that the first surface (rough) is on the outer of a nerve, while the second surface (smooth) is on the inside against the nerve surface.

The amount of overlap will depend upon a number of factors known to the surgeon and others skilled in the art, but sufficient amount of overlap is required to allow at least a portion of the plurality of protruding collagen bundles to engage with at least a portion of the plurality of apertures on the second surface. This arrangement enables the collagen bundles to engage with the apertures with little to no physical pressure (minimal) i.e. the first surface and the second surface of the pliable collagen membrane are held together (self-attach) by the engagement of the protruding collagen bundles with the apertures. In some embodiments, the overlap is at least 10%, while in other embodiments the overlap is at least 20%. In some embodiments, the degree of overlap is selected from the group consisting of 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59% and 60%.

In some embodiments, the first surface and the second surface of the pliable collagen membrane interlock to provide a stronger engagement. Thus, as described herein, the devices of the present invention are able to form a self-engaging attachment without the need for sutures or other attachment means once positioned on the nerve and/or epineurium. This is particularly the case when the pliable collagen membrane is applied in vivo, which is typically a "wet" environment. That said, the pliable collagen membrane is also amenable for use with sutures for holding it in place once positioned on the nerve if required by the surgeon.

The term "suture" is used herein merely for literary convenience. This term should not be construed as limiting in any way. The embodiments of the subject invention could be utilized with any of a variety of devices, substances, and techniques useful for securing and/or connecting nerve tissue. This can include, but is not limited to, sutures, staples, vascular clips, hydrogels, fibrins, urethane-based adhesives, and other medical adhesives, or combinations thereof.

The phrase "allowing said device to remain in place" refers to attachment of the device of the present invention to the nerve or epineurium that requires repair together with the period of time that the device is attached to the nerve and/or epineurium.

The term "period of time" as used herein refers to time taken for the device of the present invention to become successfully integrated, as defined herein, into the nerve or epineurium to which it was attached. In some embodiments, the period of time is less than 4 weeks. In some embodiments, the period of time is between 2 weeks and 4 weeks.

The length of the device can vary depending upon a variety of factors that are understood by those with skill in the art, including, but not limited to, the length of the damaged or severed nerve, the diameter of the damaged or severed nerve (or if a donor nerve is being used the donor nerve diameter), where and how many sutures can be used, and the in vivo location of the severed or damaged nerve, as well as other factors. In one embodiment, the length of the device is between approximately 0.5 cm and approximately 3.0 cm. In a more particular embodiment, the length of the device is between approximately 0.75 cm and approximately 2.0 cm. In a specific embodiment, a device has a length of approximately 1.0 cm.

In some embodiments of the present invention, the methods and devices are used in nerve transfer in vivo. This might require the removal of all, or part, of a damaged nerve in a recipient patient. Once the damaged nerve has been removed a graft can be used to restore function to the nerve. Various types of graft are encompassed within the subject invention, such as autografts, syngrafts, allografts, and xenografts. The size (e.g., length and diameter) of the graft is not critical to the subject invention. For example, the length of the nerve graft can be from about 1 cm to about 10 cm, or over about 10 cm. The diameter of the nerve graft can match that of any injured nerve or part of a nerve, as needed. The nerve graft can be a structurally complete segment of nerve to bridge a gap along the length of the recipient's nerve or to replace the distal end, i.e., for end-to-end grafting. Alternatively, the nerve graft can be a partial nerve segment, or eccentrically-shaped (e.g., a nerve flap), and intended to reconstruct a lacerated nerve that has some structural disruption, but retains its physical continuity.

Once a donor nerve is placed into the defect site end-to-end with the recipient nerve stump and positioned correctly one or more sutures can be used to hold these in place until the repair device of the present invention is wrapped around the defect site. Alternatively, this procedure could be accomplished without the use of sutures i.e. merely wrapping the device of the invention around the donor and recipient nerves.

Optionally, a tissue adhesive, such as a biological glue is applied to the donor and recipient nerve stumps. Preferably, the biological glue is a fibrin-containing adhesive, such as fibrin glue, fibrin sealant, or platelet gel. Biological glues are well known in the surgical art (Suri A et al. Neurol. India 50:23-26: Alibai E et al. Irn J. Med. Sci. 24(3&4):92-97: Sames M et al. Physiol. Res. 46(4):303-306: Jackson M et al. Blood Coag. Fibrinolysis 7:737-746; Fasol R et al. J. Thorac. Cardiovasc. Surg. 107: 1432-1439). As used herein, the terms "fibrin glue", "fibrin sealant", and "fibrin tissue adhesive" are used interchangeably to refer to a group of formulations containing fibrinogen and thrombin, which lead to the formation of a fibrin clot at the site of application.

The invention also includes kits for use in the repair of severed or damaged nerve or epineurium. Such kits can be used for laboratory or for clinical applications. Such kits include a device as described herein, and instructions for applying said device to repair a patient's epineurium. The kits can include a container for storage, e.g., a light-protected and/or refrigerated container for storage of the device. Optionally, a kit can include additional agents for use in epineurium repair e.g. an antibiotic, suture material and the like.

The kits described herein can also include a means to apply the device to an epineurium, for example, forceps, suture needle, fibrin glue and the like. Kits can further include accessory tools for tissue approximation e.g. clips, standard weights, aspiration apparatus, and compression gauges.

Kits can include instructions for use.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples are intended to be illustrative only i.e. not limiting, since numerous modifications and variations therein will be apparent to those skilled in the art. All percentages are by weight and all solvent mixture proportions are by volume unless otherwise noted.

Example 1 Pliable Collagen Membrane Preparation

A collagen segment from porcine inner organ lining was carefully separate and placed into a solution comprising about 70% ethanol and allowed to briefly incubate at room temperature. The collagen-containing tissue was then stretched fatty side up over the working surface and as much fat tissue and blood vessels as possible was removed.

In order to visualize fat tissue present the collagen-containing tissue was coated with glycerol for about 10 minutes. At which point the collagen was transparent, but the fat tissue was a white colour. Using forceps the white fat tissue was separated from the collagen under an anatomical microscope.

When complete, the collagen-containing tissue was carefully transferred to a sealed container and incubated in a solution comprising about 1% (v/v) sodium dodecyl sulphate (SDS) and 0.2% (v/v) lithium chloride (LiCl) in order to denature the non-collagenous proteins. The incubation was left overnight at 4.degree. C.

The collagen-containing tissue was then carefully washed two times in 100% acetone to remove the denatured non-collagenous proteins. The tissue was then centrifuged at 100 RPM in a 200 ml container in order to gently spin down residual solutions, non-collagenous proteins and nucleic acids from the collagen-containing tissue.

The collagen-containing tissue was carefully removed and once again washed in Steripure™ water 3 times. Optionally, the collagen-containing tissue was washed in a solution comprising NaOH: NaCl after which it was centrifuged at 100 RPM for 90 minutes.

The collagen-containing tissue was then immersed in 0.5% (v/v) HCl and placed on shaker for 30 minutes to denature the collagen. It was found that the concentration of HCl and incubation time was important in order to avoid damaging the mechanical structure of the resulting pliable collagen membrane.

The collagen-containing tissue was then removed and once again washed in Steripure™ water 3 times.

The collagen-containing tissue was then neutralized using 0.5% (v/v) NaOH. At this stage preliminary testing of the mechanical properties of resulting pliable collagen membrane could be undertaken.

The pliable collagen membrane was then manipulated using mechanical forces (compression and extension) using a stainless-steel frame. Once the pliable collagen membrane was stretched to the right size, thickness (e.g. less than 200 microns, preferably less than 100 microns, even more preferably less than 70 microns) and the like, the tissue was denatured in situ i.e. within the frame, immersion in a solution comprising 1% (v/v) HCl. Typically, the tissue was incubated with shaking at 100 RPM for 22-25 hours until the collagen fibre bundles had aligned.

The pliable collagen membrane was then washed with water and rinsed with mixture of 1% (v/v) SDS and 0.2% (v/v) LiCl.

Finally, the pliable collagen membrane was treated with acetone and air-dried while still stretched within the frame so that the protruding collagen bundles on the rough surface of the collagen membrane became fixed. The pliable collagen membrane was then stretched, compressed and/or rolled to create a smooth surface on the opposite side of the membrane (second surface). The finished pliable collagen membrane was then examined and cut to size using a laser cutter.

Example 2 Nerve Transfer

Nerve transfers have recently transformed standard of care on adaptation of physical and mental disability to gain of function care. Studies have shown that nerve transfers alone or in conjunction with tendon transfer has enabled small gains in function of basic daily activities. This has made "game changes" in patients with SCI, in particular tetraplegia.

In patients with tetraplegia, nerve transfer is used as a "bypass" to the spinal cord injury. When spinal cord injury occurs, there are three separate damaged regions. Above the level of the injury, both the upper motor neuron and lower motor neurons are intact and continue to function. At the level of the injury both upper and lower motor neurons were damaged. The involved nerve axons will undergo Wallerian degeneration and pathological changes in the neuromuscular junction. However, below the level of the injury, there is no injury to the lower motor neurons, but there is loss of function due to loss of the upper motor neurons. Due to the fact that there is not an injury to the peripheral nerve (lower motor neuron), Wallerian degeneration on axons does not occur within the peripheral nerve. These peripheral nerves are not damaged and a nerve-muscle connection often remains intact at the motor end plates. Nerve transfer utilises functioning nerves supplied above the level of the spinal cord injury as donors to innervate muscles supplied by nerves originating from the level of the injury or below. During nerve transfer procedures, the injured peripheral nerve (recipient) is reconnected with the spinal cord by redirection of a functional peripheral nerve (donor). The donor nerve is severed, and the "live" stump (i.e., the end still connected to the spinal cord) is joined to the distal stump of the recipient nerve. Regenerating axons from the donor nerve grow into the endoneurial tubes of the recipient nerve and unite with receptors on the recipient nerve's target organs, restoring connectivity to the spinal cord and brain.

Nerve transfer procedures can restore function to the elbow, wrist, fingers, and thumbs. As there is greater redundancy in peripheral nerves compared to muscles, there is a larger pool of donors for nerve transfer compared to tendon transfer. This allows the surgeon to reduce the distance required for axon regeneration by selecting a donor that can be joined to the recipient close to the recipient's target organs, thereby increasing the likelihood of treatment success.

Advantages of nerve transfer over tendon transfer for people living with tetraplegia are the ability to restore sensory function, and lack of functioning muscles below the elbow does not preclude treatment. Nerve transfers avoid the mechanical challenges of tendon transfer such as intraoperative tendon tensioning and post-treatment failure due to tendon rupture, adhesions, or excessive stretching. They are an elegant and efficient solution to restore of motor function because the resultant movement is powered by the muscle anatomically designed for that function, preserving natural biomechanics and range of motion, and providing superior dexterity and control compared to tendon transfer. Participants in a clinical study who received both types of transfer reported that hands treated with tendon transfer felt stronger, but hands that received nerve transfer had a more natural appearance, were more supple for social interactions, had greater dexterity, and were better at grasping large objects and using electronic devices.

A search of the PubMed database (November 2020) provided 12 clinical studies of nerve transfer in tetraplegia that included data on motor recovery using the MRC grading scale for muscle function (Table 1). There were no controlled trials, and eight studies were case reports describing outcomes in a single patient. MRC data was extracted for nerve transfers performed to restore function to the elbow (triceps), hand grip/release (finger flexion/extension), and thumb pinch/release (thumb flexion/extension). Participants were considered to have achieved functional motor recovery (FMR) if muscle function recovered to MRC grade 3 or better Roganovic.

TABLE 1

Standardised Criteria for Assessment of Recovery
of Motor Function after Nerve Repair Surgery

| Treatment Response MRC Score | Interpretation Functional motor recovery (FMR) |
| --- | --- |
| M5 | Normal power (unlikely for injuries requiring nerve transfer) |
| M4 | Active movement against gravity & resistance |
| M3 | Active movement against gravity Non-responder |
| M2 | Active movement with gravity eliminated |
| M1 | Flicker or trace of contraction |
| M0 | No contraction |

A total of 56 study participants received 132 nerve transfers, of which 70 transfers were performed to restore two muscle functions (finger+thumb extension, or finger+thumb flexion), for a total of 202 muscle functions. Meta-analysis showed that the pooled functional motor recovery rate was 61.9% (95% CI 55.2-68.6) at a mean assessment time of 22.0 months (SD 6.0, range 6-24.9) post-treatment. Finger extension was the most successful reconstructive procedure with 81.8% of transfers achieving FMR (95% CI 68.6-59.0) at 21.6 months after surgery and thumb flexion the least, with 46.2% of transfers achieving FMR (95% CI 30.5-61.8) 22.8 months after surgery (Table 2). These data indicate that nerve transfer is a feasible approach for surgical reconstruction of arm and hand function and that development of new technologies to improve the consistency and predictability of treatment outcomes is needed.

TABLE 2

Functional Motor Recovery (FMR) in Studies of Nerve Transfer for
Restoration of Arm and Hand Function in Patients with Tetraplegia

| Muscle Function | N (studies) | N (transfers) | Months (mean) | % FMR (95% CI) |
| --- | --- | --- | --- | --- |
| Elbow (triceps) | 7 | 23 | 20.9 | 73.9 |
| (finger flexion) Hand release | 8 | 76 | 21.6 | 51.3 |
| (finger extension) Thumb pinch | 6 | 33 | 22.0 | 81.8 |
| (thumb flexion) Thumb release | 7 | 39 | 22.8 | 46.2 |
| (thumb extension) | 5 | 31 | 23.0 | 77.4 |
| All functions | 20 | 2 | 22.0 | 61.9 |

Although restoration of arm and hand function is the most desired therapeutic goal for people with tetraplegia, reconstructive surgery is underutilised. It has been estimated that up to 75% of people with tetraplegia could benefit from reconstructive surgery to improve arm and hand function. In a recent US survey, less than 50% of patients had been informed about the existence of reconstructive surgery, and only 9% of patients in the survey received surgical treatment.

Reasons for underutilisation of reconstructive surgery are multifactorial. The main barriers for wider uptake appear to be lack of referrals to specialist surgeons, especially given the limited window for restoration of motor function after nerve injury, and lack of knowledge and collaboration regarding reconstructive procedures within the US healthcare system. An additional issue is the lack of US surgeons willing or able to perform nerve transfer procedures. Only three of the twelve published studies of nerve transfer in tetraplegia were performed in US, and all were conducted by the Washington University School of Medicine. The majority of reconstructions performed in the US are tendon transfers, which are simpler procedures compared to nerve transfer, but are more limited in restorative scope, require patients to have fully functioning arm muscles for use as donors, and are less attractive to patients as they require extended immobilisation and physical rehabilitation of the operative limb.

Nerve transfer is a promising reconstructive procedure intended to restore arm and hand function in patients with tetraplegia. However, published studies of nerve transfer in people with tetraplegia have identified that further investigation is needed into improving predictability in treatment outcomes, treatment outcomes at extremes of patient age, optimal timing after injury, and the utility of nerve transfer in patients who are more than 24 months post-injury.

While the use of nerve transfers in patients with tetraplegia is promising in treatment of upper limb paralysis, the assessment, selection, and timing of appropriate nerve transfer are always complex. One of the key impacts of successful nerve transfer is that the surgical procedure must be able to reconnect the function nerve from different region of spinal cord to a dis-functional nerve originally from the death neuron in the spine. To do so, it will require the surgical procedure that can provide sufficient protection and microenvironment for remyelination and nerve axon extension and reconnection soon after surgery.

Epineurium, the outer layer of dense irregular connective tissue surrounding the peripheral nerve is an extension of spinal dura mater. Under normal physiological condition, epineurium acts as an anatomical barrier of the peripheral nerves, protects nerve stretch injury and provides nutrients for nerve grow. Epineurium surrounds multiple nerve fascicles and contains blood vessels which supply the nerve. There are two distinct layers of epineurium. The most outer one is made of connective tissue with vascular components. The inner sheath consists of collagen fibrils and collagen fibres. The epineural areola also contains fibroblasts, variable amount of fat, and hyaluronic acid. Human epineurium constitutes up to 70% of the cross sectional of the peripheral nerve and contains collagen type I and III.

An ideal situation for successful nerve transfer procedure is to re-establish a barrier structure similar to epineurium for nerve transfer at the site. However, current gold standard surgical procedure of nerve transfer in treatment of upper limb paralysis, only used sutures onto epineurium to connect the end-to-end nerves. Some surgeons may apply fibrin sealant locally to provide a haemostatic barrier for nerve transfer. In most of cases, it is still far from reach to meet the ideal situation of introduction of epineurium barrier structure. Although there are several attempts on the development of autologous epineurium conduit for nerve repair, it is almost impossible for patients with paralysis to receive autologous epineurium tissue for nerve transfer.

Figure 3:
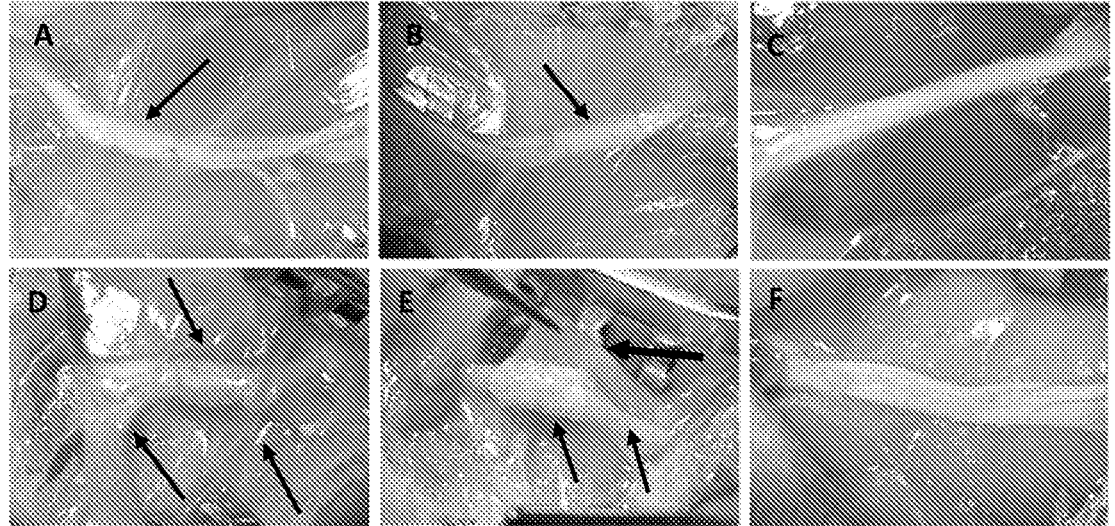
FIG. 3 shows rat model of peripheral nerve injury—4 weeks post-treatment A&B) nerve repair with nerve repair device of the present invention: C) nerve repair device of the present invention control (unoperated contralateral side): D&E) FDA-cleared collagen nerve device (NEURA-WRAP™): F) FDA-cleared device (NEURAWRAP™) control (unoperated contralateral side). White arrows—nerve device: green arrows—adhesion of nerve device to surrounding soft tissue.

An alternatively approach is to use nerve repair devices, that have been developed to assist in nerve repair surgery. Current nerve repair devices (either a hollow tube or a sheath) are composed of either polymers or reconstituted collagen (Table 3).

the animal (FIG. 3 C). The nerve repair device of the present invention appeared to be well integrated into the epineurium and did not protrude. There was no scar tissue or fibrous adhesion of the nerve to the surrounding soft tissue. In contrast, repair sites in the animals that received the FDA-cleared collagen device (NEURAWRAP™) showed extensive thick, dense connective tissue that covered the surface

TABLE 3

| Commercially available FDA-approved nerve conduits | | | |
|---|---|---|---|
| Product name | Material | Structure | Company |
| NeuraGen ® | Collagen Type I | Semipermeable, fibrillar structure of the collagen | Integra LifeSciences Co, Plainsboro, NJ, USA |
| NeuroFlex ™ | Collagen Type I | Flexible, semipermeable tubular collagen matrix | Collagen Matrix, Inc., Franklin Lakes, NJ, USA |
| NeuroMatrix ™ | Collagen Type I | Semipermeable tubular collagen matrix | Collagen Matrix, Inc. |
| NEURAWRAP ™ | Collagen Type I | Longitudinal slit in the tubular wall structure | Integra LifeSciences Co |
| NeuroMend ™ | Collagen Type I | Semipermeable collagen wrap designed to unroll and self-curl | Collagen Matrix, Inc. |
| Neurotube ® | Polyglycolic acid | Absorbable woven PGA Mesh Tube | Synovis Micro Companies Alliance, Birmingham, AL, USA |
| Neurolac ™ | Poly (D,L-lactide-co-ε-caprolactone) | Synthetic and transparent PLCL tubular structure | Polyganics BV, Groningen, Netherlands |
| Salutunnel ™ | Polyvinyl alcohol | Non-biodegradable PVA tubular structure | Salumedica LCC, Atlanta, GA, USA |

Abbreviations: FDA, Food and Drug Administration; PGA, poly(glycolic acid); PVA, polyvinyl alcohol; PLCL, poly(ε-caprolactone-co-lactide).

While these nerve repair devices have been shown to be effective for common peripheral nerve injuries, they are almost unsuitable for use in nerve transfer surgery in treatment of upper limb paralysis because of inability to introduce an epineurium barrier structure. According to the literature, most of them suffer from issues of poor biocompatibility (cause adhesions, scar tissue formation and neuroma), are too rigid to be manipulated easily, and they cannot be adapted to different sized nerves if the donor nerve is a different size to the recipient nerve. Literature review showed that there are no published studies using nerve repair devices to restore peripheral nerve function in patients with tetraplegia.

To address the unmet medical need of nerve transfer in patients with paralysis, Applicant developed a repair device comprising a pliable collagen membrane as discussed in Example 1 that mimics the native structural, physiological and biological performance of epineurium. Pre-clinical performance test showed that the device of the present invention has adequate mechanical properties, semi-permeability, and appropriate degradation kinetics structure to allow for Schwann cell migration and axon outgrowth.

Figure 2:
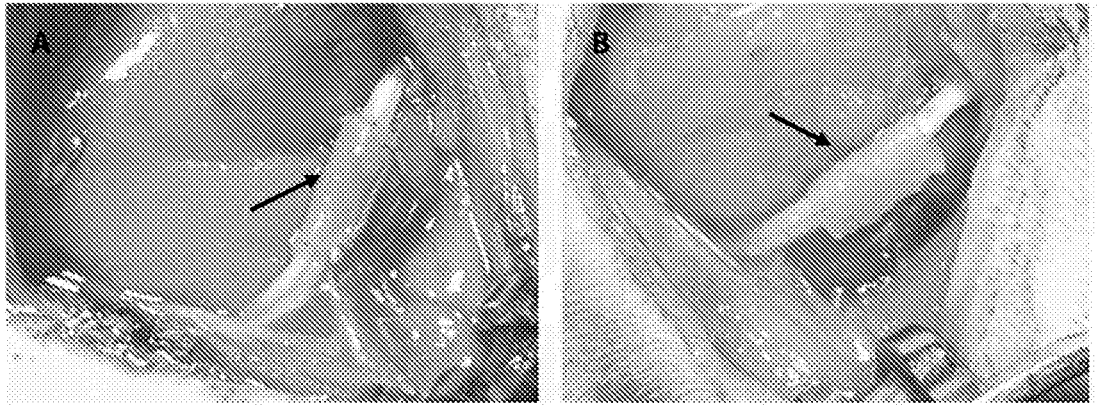
FIG. 2 shows the deployment of A) nerve repair device of the present invention and B) FDA-cleared collagen nerve device (NEURAWRAP™) in a rat model of peripheral nerve injury. White arrows—implanted devices.

Proof of concept evidence was obtained from a preclinical study using a rat model of peripheral nerve repair. The sciatic nerve was completely transected, then repaired with three epineurial microsutures, consistent with normal surgical practice in human procedures. Suture repairs that were rated as excellent or good were encased in either the repair device of the present invention or a commonly used FDA-cleared collagen nerve device (NEURAWRAP™). The position of the devices was marked using a non-absorbable "stay" suture at each end of the device to attach it to the epineurium (see, for example, FIGS. 1 and 2).

After 4 weeks of healing, the repair sites in the two animals that received treatment with the nerve repair device of the present invention (FIGS. 3A & B) were similar in appearance to untreated nerves on the contralateral side of of the nerve device and caused it to adhere to the surrounding soft tissue (FIGS. 3 D & E). NEURAWRAP™ did not appear to be integrated into the epineurium and remained bulky in appearance compared to the untreated nerves on the contralateral side (FIG. 3 F).

Figure 4:
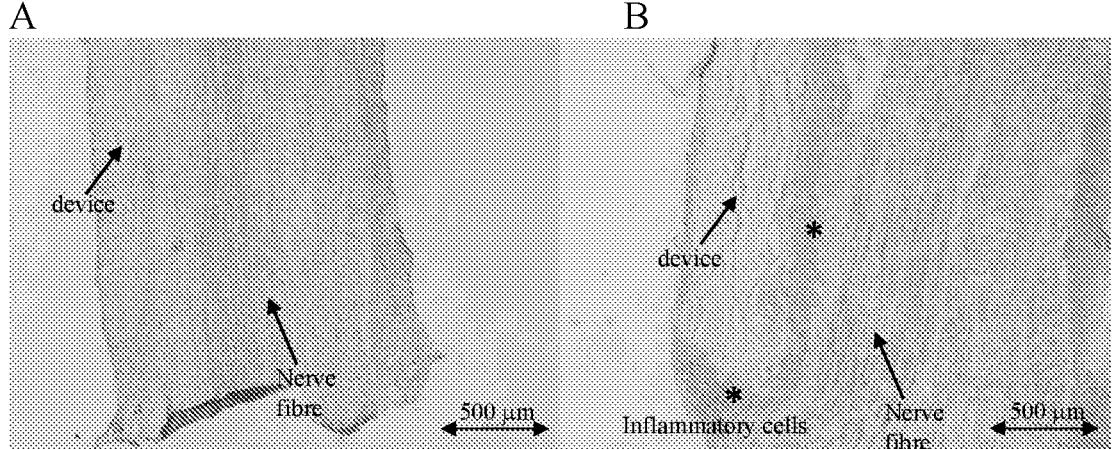
FIG. 4 shows H&E stain of nerve tissue from rat peripheral nerve injury study. A) nerve repair device of the present invention: B) FDA-cleared collagen nerve device (NEURA-WRAP™). Black scale bar=500 μm Blue arrows—device: green arrows—nerve fibres: yellow stars—inflammatory cells.

Histological examination was consistent with gross examination for the nerve repair device of the present invention. Histologically it was revealed that new, vascularised epineurium-like tissue had formed of at the nerve repair site (FIG. 4A). There was no evidence of inflammatory reaction. Collagen fibres from the nerve repair device of the present invention were well integrated into the epineurium-like tissue and were similar in appearance to normal connective tissue. Abundant neurofilaments were detected by immunohistochemistry, adjacent to the new epineurium tissue, and well-organised nerve fibres were observed distal to the nerve repair, evidence of successful axon regeneration across the repair site. In contrast, the repair sites of the FDA-cleared collagen device (NEURAWRAP™) were encapsulated with fibrous tissue, causing axon entrapment and nerve compression (FIG. 4 B). Infiltration of lymphocytes, plasma cells, macrophages, and foreign body reactive multinuclear giant cells was observed at the repair site, evidence of inflammatory reaction. Neurofilaments and axon growth were observed on the distal side of the repair, but the newly regenerated nerve tissue was less organised compared to our product repair sites.

The results from this study showed that treatment with the nerve repair device of the present invention resulted in formation of new epineurium-like tissue at the repair site. No inflammation, nerve compression, or axon entrapment were observed, and use of our product provided an environment suitable for axon regeneration across the repair site.

Example 3 Clinical Study: Use of the Nerve Repair
Device of the Present Invention to Improve
Outcomes of Nerve Transfer Surgery to Restore
Arm and Hand Function in Patients with
Tetraplegia Based on the preclinical observation, Applicant conducted a prospective case series, clinical study CG-006, to investigate the use of the nerve repair device of the present invention to improve the outcomes of nerve transfer in patients with tetraplegia. Fourteen nerve transfers were performed to restore arm and hand function in four patients with tetraplegia. Recovery of motor function was assessed using manual muscle testing and graded using the British Medical Research Council (MRC) standardised criteria for motor function, for up to two years post-treatment (Table 1 infra).

Figure 5:
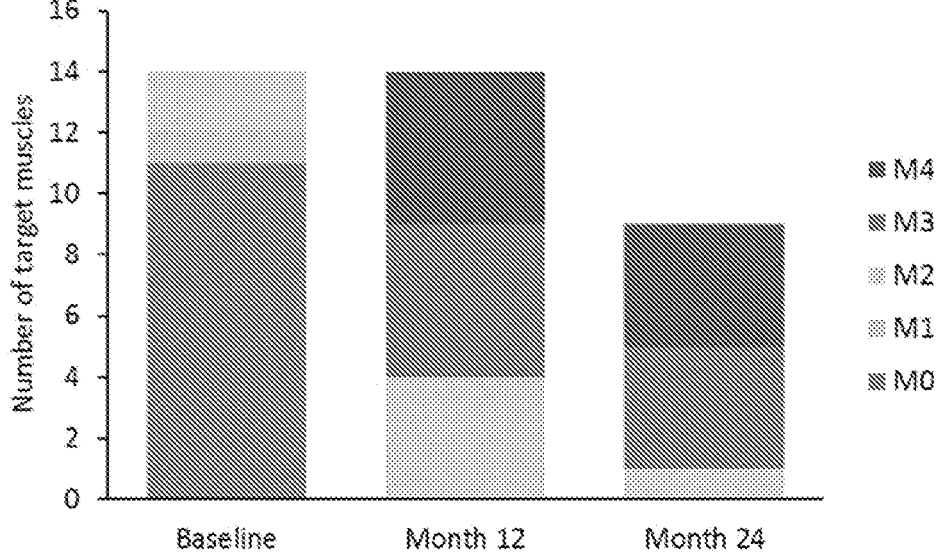
FIG. 5 shows motor recovery after nerve transfer to improve arm and hand function in people with tetraplegia. Recovery to M3 or better is classified as functional motor recovery (FMR).

Functional motor recovery of previously paralysed muscles was observed in 71.4% of transfers at 12 months post-treatment, increasing to 88.9% at 24 months post-treatment (FIG. 5). In comparison, meta-analysis of nerve transfer surgery (with suture repair only) in people with tetraplegia resulted in FMR of 61.9% from 202 nerve transfers at 22 months post-treatment (Table 4).

TABLE 4 comparison of functional motor recovery after standard
nerve transfer surgery (suture only) vs repair incorporating
the repair device of the present invention

| Nerve repair | Repair | N (transfers) | Time (months) | % Functional Motor Recovery |
|---|---|---|---|---|
| Tetraplegia | Suture only | 202 | 22.0 | 61.9% |
| Tetraplegia | Repair Device | 14 | 12/24 | 71.4/88.9% |

Loss of elbow extension affects approximately 75% of people with tetraplegia. Restoration of elbow stability and function are essential for the ability to self-transfer (e.g., from bed to wheelchair), perform pressure-relieving activities, balance while sitting, reach for overhead objects, and operate a manual wheelchair.

Figure 6:
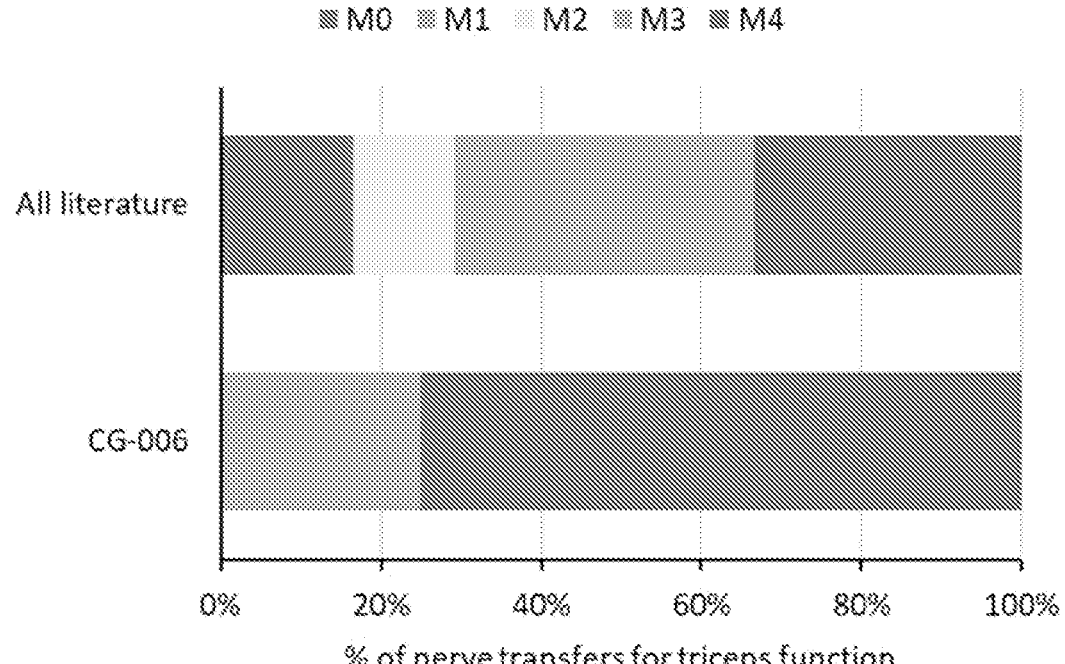
FIG. 6 shows recovery of triceps function in CG-006 compared to published studies of nerve transfer in people with tetraplegia.

Elbow extension is provided by the triceps muscle. Functional recovery of triceps muscle was observed 100% of patients treated using the nerve repair device of the present invention at 12 months after nerve transfer, compared to 73.9% recovery at 21 months reported in published studies (FIG. 6, Table 5). Participants in the clinical study were able perform a range of daily activities that were not possible before receiving study treatment, such as being able to move around and roll over in bed, use a manual wheelchair, and independently transfer from bed to wheelchair using a slideboard.

The nerve repair device of the present invention demonstrated faster and better results in restoring triceps muscle function, compared to data from studies of normal nerve transfer surgery. This level of recovery would not be possible using standard of care treatments for tetraplegia (physical rehabilitation).

TABLE 5 recovery of triceps function in CG-006 compared to published
studies of nerve transfer in people with tetraplegia.
FMR = functional motor recovery (% of patients achieving
M3 score or better on motor function assessment)

| Study | Time (months) | FMR (%) | N (transfers) |
|---|---|---|---|
| CG-006 | 12 | 100 | 4 |
| Literature (pooled) | 20.9 | 73.9 | 23 |
| Van Zyl 2019 | 24 | 80 | 10 |
| Fox 2015 | 12 | 0 | 1 |
| Khalifeh 2019 | 24.9 | 50 | 6 |
| Bertelli 2011 | 14 | 100 | 2 |
| Bertelli 2012 | 12 | 100 | 1 |
| Van Zyl 2014 | 19 | 100 | 1 |
| Sananpanich 2018 | 10 | 100 | 2 |

Overall, these data support the position that the nerve repair device of the present invention can act as an epineurium substitute and enable the repair of peripheral nerve.

Example 4 Evaluation of Nerve Repair Device in
Reconstruction of Upper-Extremity Peripheral
Nerve Injuries Scanning Electron Microscopy (SEM), Transmission electron microscopy (TEM) and enhanced micro-computed tomography (micro-CT) were used to examine the ultrastructural characteristics of the nerve repair device of the present invention. A prospective case series with 2-year follow-up was undertaken and reported. Nerve reconstructions were conducted for patients who required nerve transfers or grafts. Participants underwent single or multiple nerve reconstructions in one or both upper limbs.

Methods

Structural Characterization

All analyses were performed at the Centre for Microscopy, Characterization and Analysis at The University of Western Australia. For SEM assessment, 1 cm x1 cm squares of the nerve repair device of the present invention were mounted on a stub and sputter-coated with a layer of platinum (Pt). Samples were analyzed using a Zeiss 1555 VP-FESEM (a high-resolution, field-emission variable-pressure scanning electron microscope). For micro-CT assessment, the nerve repair device of the present invention was first stained with 0.3% potassium iodine solution as a contrast agent for viewing of soft tissues under micro-CT and 3D image reconstruction was performed using XM Reconstructor software, v10.7.3679.13921, Zeiss. These staining techniques provided a high-resolution image without damage to the sample.

Clinical Study Design and Participants

A prospective case series of 19 patients with 2-year follow-up was undertaken and reported in accordance with the PROCESS guidelines. The study received approval from the Human Research Ethics Committee of St John of God Health Care and was registered with the Australian and New Zealand Clinical Trials Registry (ACTRN12616001157460). As according to Seddon classification of peripheral nerve injuries, we selected patients with neurotmesis in which the injured nerves lost the disconnection with resultant complete functional loss. Inclusion criteria were males and females aged 18-50 years with traumatic injury to one or more peripheral nerves of the upper limb or hand in the previous 18 months.

Surgical Intervention

Nerve reconstructions were conducted for patients who required nerve transfers or grafts. Participants underwent single or multiple nerve reconstructions in one or both upper limbs. Major reconstructions include triceps nerve transferred to axillary nerve in the shoulder: the posterior axillary nerve to biceps or triceps nerves, or gracilis nerve to biceps nerves in the elbow: supinator or *brachialis* nerve to anterior, median or posterior interosseous nerves, or extensor carpi radialis nerve to posterior interosseous nerves in the hand. All surgical procedures were performed by a single surgeon (AOB). Surgeries were conducted under general anaesthesia with muscle relaxants and thromboprophylaxis, with the patient positioned as required for the most suitable surgical approach.

Donor and recipient nerves were identified with use of a nerve stimulator and locator device and dissected away from surrounding fascia. Nerve stumps were coaptated with two anchored sutures using 8-0 nylon for larger nerves or 10-0 nylon for smaller nerve stumps. The nerve repair device of the present invention was placed under the coaptation site with the rough side (first surface) facing up. The nerve repair device was then wrapped around the coaptation site, with at least 1.5 cm coverage across proximal and distal stumps of the nerve, and then wrapped with minimum 30% overlay to create an interlocking adhesive contact between the rough (first surface) and smooth surface (second surface) of the nerve repair device. This ensured adequate contact between nerve repair device and the nerve regardless, of the size mismatch between donor and recipient nerve as well as mechanical protection of the nerve from soft tissue compression. Fibrin sealant (TISSEEL, Baxter, Deerfield, IL, USA) was placed around the nerve repair device to stabilize its position around the nerve.

The operated limb(s) were protected in a sling for 1-2 weeks post-operatively to safeguard the coaptation site. All post-operative therapy was done in an outpatient setting.

Outcome Assessments

A physical examination of the affected limb was conducted at baseline and at each post-operative clinic visit by an appropriately qualified investigator. Efficacy endpoints including functional assessment and patient reported outcomes were described using the following:

Motor Function

The British Medical Research Council (MRC) grading system is used for grading of muscle power as an assessment of motor function via manual muscle testing. The MRC scale has been demonstrated to have substantial inter- and intra-rater reliability for the upper limb, and is suitable for use even where extreme muscle weakness exists.

Sensory Function

Tactile gnosis is the ability to recognize the properties of objects through touch (e.g., texture), and is a key indicator of sensory function. Static two-point discrimination (s2PD) and moving two-point discrimination (m2PD) testing was used for determination of sensory function. s2PD and m2PD is an assessment tool that tests the ability of the patient to discern the shortest distance between 2 points that can be perceived as being separate. Normal values for the fingers were less than 6 mm for static 2PD and 2-3 mm for moving 2PD. The static test measures the innervation density of slowly-adapting nerve receptors, while the moving test measures quickly-adapting nerve receptors.

QuickDASH

The QuickDASH (Quick Disabilities of the Arm, Shoulder and Hand) questionnaire is a validated outcome measure of symptoms and disability in patients with musculoskeletal disorders of the upper limb. Eleven items are scored on a five-point scale from 1 (no difficulty) to 5 (inability to perform a task). The raw score is scaled to a final score out of 100, with a higher score representing greater disability. The optional work-specific module, which consists of a further four questions, was also administered for this study.

Visual Analogue Pain Scale (VAS)

Pain is a common outcome after peripheral nerve injury and contributes significantly to disability. Paradoxically, both reduction and increase in pain can be associated with nerve regeneration after surgical repair. Participants' experience of overall pain, pain at night and activity-related pain was assessed using a standardized numerical visual analogue scale from 0 (no pain) to 10 (worst pain ever).

Assessment of Quality of Life (AQoL-6D)

The AQOL-6D is a validated, health-related, multi-attribute utility quality of life instrument. Participants completed a questionnaire consisting of 20 items spread over 6 dimensions, with each item given a score from 0 (death) to 100 (perfect health).

Adverse Events

All adverse events and serious adverse events were monitored and recorded.

Data Management and Analysis

The study was conducted in accordance with the approved protocol, GLP and all applicable regulatory requirements. Assessments were recorded on individual case report forms and data was managed using the Research Electronic Data Capture tool, hosted at St John of God Hospital, Subiaco, Western Australia. Monitoring queries were generated and clarification was sought, if required, from the responsible Investigator or delegate at each site.

Data from patient reported outcomes were imported into SPSS (v27) for statistical analysis. A one-way repeated measures ANOVA was performed using time point as the within-subjects factor. Greenhouse-Geisser correction was applied to datasets that returned significant results for Mauchly's Test of Sphericity. Post-hoc testing was performed (where applicable) using Bonferroni correction. MRC scores were reported as median and interquartile range (IQR)

Results

Structural Characterization of the Nerve Repair Device of the Present Invention To examine if the nerve repair device of the present invention mimics the bilayer structure of epineurium Applicant studied the morphological features of the pliable collagen membrane using SEM, enhanced micro-CT, and TEM. Enhanced micro-CT showed that nerve repair device consists of two distinct layers, an outer layer (first surface) containing dense and parallel collagen bundles and an inner layer (second surface) containing lose bundles and fibres (some of which were vertically distributed along the pliable collagen membrane). D-spacing of collagen fibrils was present in the nerve repair device. The thickness of nerve repair device was approximately 100 μm, with mean diameter of collagen fibrils of 90 nm+/−20 nm.

Patient Demographics

A total of 19 participants (17 males and 2 females) qualified for inclusion in this study. Five participants had a cervical spinal cord injury and were candidates for nerve transfer surgery to restore upper limb function. Eight patients had traumatic injury to the brachial plexus requiring reconstructive surgery to primarily restore shoulder or elbow function. Six patients had upper limb peripheral nerve injuries requiring surgery to restore shoulder, elbow, wrist, or hand function. The most common cause of injury was motor vehicle accident (60%), but other causes included, sport and recreation-related injuries, falls and iatrogenic causes. All patients were followed for 24 months post-surgery, with the exception of one participant who passed away 12 months after surgery (due to lung infection) and two patients who were lost to follow-up after 6 months.

Evaluation of Outcomes

A total of 36 peripheral nerve reconstructions were conducted, 35 for motor function and one for sensory function. Among the 36 peripheral nerve transfers, four were in the shoulders, 11 in the elbows, two in the wrists and 19 were in the hand.

Median overall MRC score on the types of nerve transfer at baseline was 0 (IQR−0: n=60). At 6 months, median MRC score improved to 1 (IQR 2: n=60), with further improvement observed at 12 months (median MRC score=3: IQR 2: n=59) and 24 months (median MRC score=4: IQR 1.25: n=48) after surgery. The reinnervation of proximal target muscles was observed in all nerve repairs assessed.

Improvements were also observed in upper limb function, as assessed by QuickDASH scores at screening (baseline), 12 and 24 month visits. Mean QuickDASH score was 52.9 at baseline (SD 20.8), with improvement to 46.8 (SD 30.2) at 24 months. Although the mean improvement in QuickDASH score was not statistically significant, 62% of participants reported an improvement in QuickDASH score at 12 months compared to baseline.

Assessment of mean pain scores for worst pain, pain at rest, pain while performing a repetitive task, and pain at night remained consistent up to 12 months. However, 77%, 46%, and 54% of participants reported a decrease in pain at this time point compared to baseline for worst pain, pain at rest, and pain at night, respectively. To investigate if pain medication had any impact on the outcomes of this assessment, Applicant analyzed patients' medication use during the study. This showed that participants were taking a median of two pain medication at baseline (mean 1.8: SD 1.56, range 0-4). These included neuroleptics, antidepressants, opioids, and non-opioid analgesics. Use of pain medication decreased to a median of one at 6 months (mean 1.4: SD 1.40; range 0-4), and zero at 12 months (mean 1.1: SD 1.55; range 0-4). Five participants reported taking no pain medication during the 12 month period, and seven participants significantly reduced or ceased their use of pain medication at 12 months, compared to baseline.

Participants completed the AQoL-6D questionnaire at screening (baseline), 12 and 24 month study visits. The results demonstrated improvements in the AQOL-6D score after surgery. Mean AQoL-6D scores remained stable out to 24 months post-treatment. However, individual improvements in AQOL-6D score were reported for 60% of participants at 6 months, and 54% of participants at 12 months.

Adverse Events

There were 9 adverse events reported in 4 participants during the study, all considered to be unrelated to the nerve repair device. One nerve repair was classified as a treatment failure at 12 months, attributed to a wound infection after surgical correction of a concomitant fracture injury. One participant passed away 12 months after surgery due to pneumonia.

Results

Figure 10:
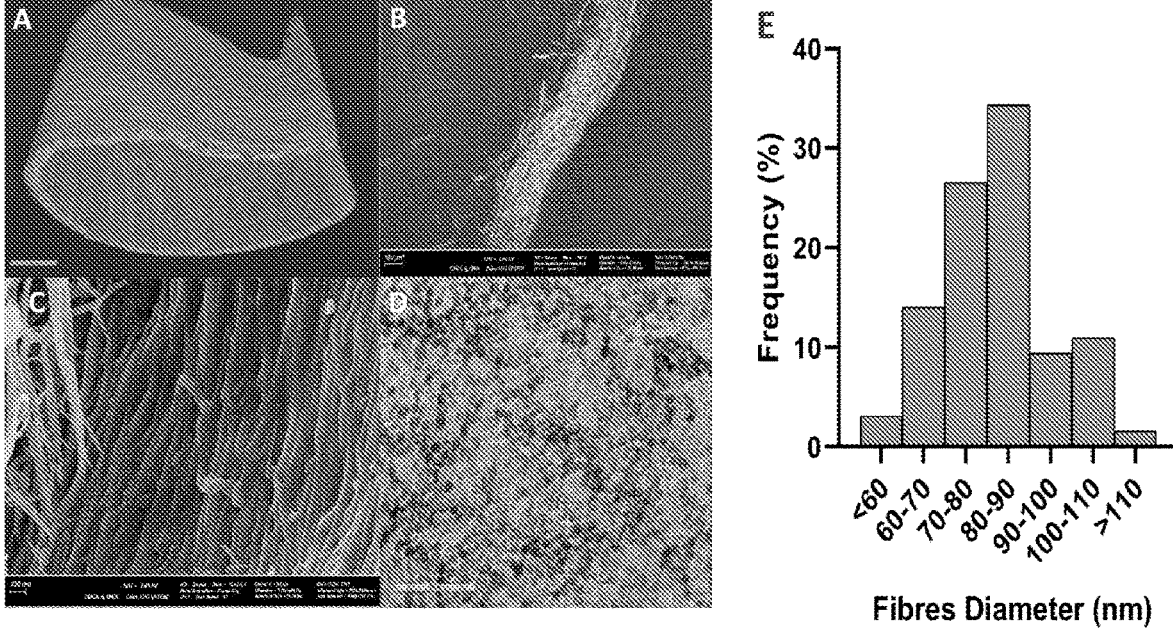
FIG. 10, Panel A shows an SEM of the pliable collagen membrane folded so that the rough (first surface) is internal and the smooth (second surface) is outer; Panel B shows the first surface (rough) in transverse: Panel C shows the alignment of the smooth (second surface): Panel D shows the spacing of collagen fibrils: Panel E shows the frequency spread of collagen fibre diameter in the pliable collagen membrane.

Morphological characterization demonstrated that the nerve repair device mimics the structural and biological properties of epineurium. The thickness of nerve repair device (100 μm) is within the range of epineurium of most human peripheral nerves (FIG. 10). A total of 36 peripheral nerve reconstructions were performed in 19 patients with upper limb nerve injuries. The results demonstrated that nerve reconstruction using the nerve repair device restored peripheral nerve function, compared to baseline, with restored motor function maintained in 90% of reconstruction at the 6 month mark. Improvement in motor function was observed in all repairs at 24 months, with 96% of reconstruction restoring active movement to target muscles.

Discussion

Patients who have lost function of their upper extremities are severely disabled. Using the nerve repair device as an aid to nerve reconstruction surgery, Applicant successfully performed 36 nerve reconstructions in 19 participants with upper-extremity paralysis due to peripheral nerve injury. Clinical assessment showed that improvements in motor function to target muscles close to the reconstruction site were observed as early as 6 months in 90% of reconstructed nerves. At 12 months, improvement in motor function was observed in all reconstructed nerves, and 97% of reconstructed nerves restored active movement to target muscles. Reduction in pain and disability were also observed at 12 months, with improvement continuing to 24 months. QuickDASH score improved in 62% of participants and 77% of participants reported a decrease in worst pain experienced. Use of pain medication decreased or ceased entirely in 77% of participants who required medication for their nerve pain at baseline.

Notably, of 19 patients with peripheral nerve reconstruction, five had C5-C8 spinal cord injuries resulting in tetraplegia. Nerve transfers performed to restore upper limb function in these patients was encouraging, with all nerve transfers aimed at restoring triceps function achieving functional motor recovery (MRC 3 or 4) after 12 months. The improvement in triceps function allowed participants to perform daily activities that were not possible before the surgery, such as being able to roll over in bed, use a manual wheelchair, and independently transfer from bed to wheelchair using a slideboard. These results compare favorably to those reported in van Zyl et al (2019), who reported a median MRC score of 3, 24 months after surgery.

While Applicant showed that significant improvements of functional outcomes on MRC score after 12 month in all of participants, pain and disability scores were not significantly different from baseline.

There are multiple factors affecting the outcome of nerve reconstruction. These include age, gender, injured nerve, time between injury and surgery, type of grafts and repaired materials used. However, comparison of outcomes between repaired materials showed that surgery using the nerve repair device of the present invention achieved relatively better outcomes than that reported in the literature. In this study, over 97% of nerve constructions resulted in functional motor recovery of target muscles at 12 months. This compares favourably with other studies showing FMR of 86% using polyglycolic acid, 76.5% using NEUROTUBE™, 75% to 88% using NEURAGEN™, and 65% using human acellular nerve graft.

CONCLUSIONS

Tetraplegia is a devastating, irreversible condition that disproportionately affects young, healthy men. People with tetraplegia have little or no voluntary control of their bowels or bladder. Their legs and torso are paralysed, and although they may have some movement left in their shoulder muscles, they have limited or absent sensation and movement in their arms and hands. People with tetraplegia have a shortened life span, and experience significant morbidity.

The US standard of care for people with tetraplegia is rehabilitation. Patients receive therapy focusing on strengthening of remaining muscle function, adoption of compensatory techniques, use of orthotic devices, and environmental modification. However, the ability of a patient with tetraplegia to regain motor and sensory function by rehabilitation alone is intrinsically limited by the extent of their spinal cord injury. Loss of connection between the brain and the peripheral nerves cannot be regenerated by physical or pharmacological therapy.

Surveys of people with tetraplegia and their caregivers have shown that regaining arm and hand function is their highest priority for functional recovery, over bowel/bladder function, walking, pain control, or sexual function. Surgical reconstruction is the most common alternative to rehabilitative therapy for chronic tetraplegia (i.e., after maximum neurological recovery is reached), and provides a means by which additional arm and hand function can be restored by strategic redeployment of residual functionality.

Nerve transfers have recently transformed standard of care of nursing assistant to gain of function care by restoring basic daily activities in patients with SCI, in particular tetraplegia. Nerve transfers recreate basic arm and hand functions for people with tetraplegia. The nerve transfer is used to "bypass" the spinal cord injury. Multiple nerve transfers can be performed in one surgical procedure, and one nerve transfer can potentially restore function to multiple muscle targets.

While ideal situation for successful nerve transfer procedure is to re-establish a barrier structure similar to epineurium for nerve transfer at the site, current gold standard surgical procedure of nerve transfer in treatment of upper limb paralysis, only used sutures onto epineurium to connect the end-to-end nerves. In most of cases, it is still far from reach to meet the ideal situation of introduction of epineurium barrier structure.

To address the unmet medical need of nerve transfer in patients with paralysis, Applicant developed a repair device comprising a pliable collagen membrane that on successful integration mimicked the native structural, physiological and biological performance of epineurium. Pre-clinical performance test showed that the repair device of the present invention has adequate mechanical properties, semi-permeability, and appropriate degradation kinetics structure to allow for Schwann cell migration and axon outgrowth. Clinical study CG-006 demonstrated that nerve transfer with the repair device of the present invention in people with tetraplegia resulted in faster and better recovery of triceps muscle function compared to studies of standard nerve transfer (suture only) from the literature.

The nerve repair device of the present invention is a technology that simplifies and increases reproducibility of the nerve transfer operative technique, reduces intraoperative handling of delicate nerve tissue, and may increase consistency and predictability of treatment outcomes. Use of the nerve repair device of the present invention would increase access to a treatment that addresses the highest functional priority for Americans living with tetraplegia.

REFERENCES

Van Zyl, N. et al. (2019), Lancet, 394(10198):565-575.
Fox, I. K. et al. (2015), Plastic and Reconstructive Surgery, 136(4):780-792.
Khalifeh, J. M. et al. (2019), JNS, 31(5):629-640.
Bertelli, J et al. (2011), J Neurosurg, 114:1457-1460.
Bertelli, J et al. (2012), J. Hand Surgery, 37(10): 1990-1993.
Van Zyl, N. et al. (2014), J. Hand Surgery, 39(9): 1779-1783.
Sananpanich, K. et al. (2018), J. Hand Surgery, 43(10): 920-926.

The invention claimed is:

1. An in vivo method of repairing severed or damaged nerve comprising:
   (i) providing a pliable collagen membrane comprising a first surface and a second surface, said first surface having a plurality of protruding collagen bundles and said second surface comprising a plurality of apertures;
   (ii) wrapping said pliable collagen membrane around at least a lengthwise portion of a severed or damaged nerve in situ at defect site so that the first and second surface contact one another and the collagen bundles on the first surface interlock with the apertures on the second surface to secure the first and second surfaces to one another, wherein said severed or damaged nerve comprises a severed or damaged epineurium, and
   (iii) allowing said device to remain in place for a period of time until said severed or damaged epineurium is repaired, which period of time will be less than 4 weeks.

2. A method according to claim 1, wherein said pliable collagen membrane is of an elongated configuration.

3. A method according claim 1, wherein said pliable collagen membrane is configured to be able to be wrapped around at least a lengthwise portion of a nerve in situ, in a manner where said first and said second surfaces are able to be placed together to self-attach to each other.

4. A method according to claim 3, wherein the pliable collagen membrane is less than 200 microns thick.

5. A method according to claim 4, wherein the nerve comprises severed or damaged epineurium, and wherein said device when wrapped around said severed or damaged nerve is capable of repairing said severed or damaged epineurium in less than 4 weeks.

6. A method according to claim 1, wherein the pliable collagen membrane comprises greater than 80% type I collagen.

7. A method according to claim 6, wherein the pliable collagen membrane further comprises type III collagen.

8. A method according to claim 1, wherein the collagen membrane forms part of a device for the in vivo repair of severed or damaged nerve, wherein the device further comprises one or more of hydroxyapatite, growth factor, chemotactic factor or extracellular matrix molecule.

9. A method according to claim 8, wherein:

the growth factor is selected from the group consisting of basic fibroblast growth factor, tumour growth factor beta, bone morphogenic protein, platelet-derived growth factor, and insulin-like growth factor;

the chemotactic factor is fibronectin or hyaluronan or combination thereof; or the extracellular matrix molecule is selected from the group consisting of aggrecan, biglycan, and decorin.

10. A method according to claim 1, wherein the repair of said severed or damaged epineurium comprises successful integration of the device into the nerve and/or epineurium without scar tissue formation or fibrous adhesion of the repaired nerve to the surrounding tissue of the patient.

11. A method according to claim 10, wherein the successful integration comprises one or more of the following:

(i) the device does not protrude from the repaired nerve;

(ii) little or no scar tissue formation at the defect site;

(iii) little or no fibrous adhesion of the repaired nerve to the surrounding soft tissue in the patient;

(iv) histological examination shows new, vascularised epineurium-like tissue at the nerve repair site;

(v) there is no evidence of inflammatory reaction following an appropriate period of time after attachment;

(vi) abundant neurofilaments are detected adjacent to the new epineurium tissue by immunohistochemistry;

(vii) well-organised nerve fibres are observed distal to the nerve repair site; and (viii) evidence of successful axon regeneration across the repair site.

* * * * *